US006409987B1

(12) United States Patent
Cardin et al.

(10) Patent No.: US 6,409,987 B1
(45) Date of Patent: Jun. 25, 2002

(54) TARGETED AGENTS USEFUL FOR DIAGNOSTIC AND THERAPEUTIC APPLICATIONS

(75) Inventors: Alan D. Cardin, Cincinnati; Cornelius L. Van Gorp, Springboro, both of OH (US)

(73) Assignee: Intimax Corporation, Cincinnati, OH (US)

( * ) Notice: Subject to any disclaimer, the term of this patent is extended or adjusted under 35 U.S.C. 154(b) by 0 days.

(21) Appl. No.: 09/544,266

(22) Filed: Apr. 6, 2000

Related U.S. Application Data
(60) Provisional application No. 60/128,139, filed on Apr. 7, 1999.

(51) Int. Cl.$^7$ ........................ A61K 51/00; A61M 36/14
(52) U.S. Cl. .................... 424/1.73; 424/1.11; 424/1.65; 424/9.1; 534/14
(58) Field of Search ............................... 424/1.11, 1.65, 424/1.69, 1.73, 9.1, 9.3, 9.4, 9.5, 9.6, 9.7, 9.8; 534/7, 10–16; 530/350

(56) References Cited

U.S. PATENT DOCUMENTS

| | | | |
|---|---|---|---|
| 3,634,123 A | 1/1972 | Eriksson et al. | 117/47 |
| 4,385,046 A | 5/1983 | Milbrath et al. | 424/1 |
| 4,440,926 A | 4/1984 | Mardiguian | 536/21 |
| 4,705,849 A | 11/1987 | Nunn et al. | 534/14 |
| 4,727,063 A | 2/1988 | Naggi et al. | 514/56 |
| 4,745,105 A | 5/1988 | Griffin et al. | 514/56 |
| 4,925,678 A | 5/1990 | Ranney | 424/493 |
| 5,013,724 A | 5/1991 | Petitou et al. | 514/54 |
| 5,108,759 A | 4/1992 | Ranney | 424/493 |
| 5,155,215 A | 10/1992 | Ranney | 534/16 |
| 5,336,762 A | 8/1994 | Ranney | 534/16 |
| 5,480,970 A | 1/1996 | Poliak et al. | 530/328 |
| 5,547,944 A | 8/1996 | Mascellani et al. | 514/54 |
| 5,552,525 A | 9/1996 | Dean | 530/326 |
| 5,561,220 A | 10/1996 | Dean et al. | 424/1.69 |
| 5,574,140 A | 11/1996 | Pollack et al. | 534/10 |
| 5,659,041 A | 8/1997 | Pollack et al. | 546/306 |
| 5,672,334 A | 9/1997 | Ranney | 424/9.34 |
| 5,707,604 A | 1/1998 | Ranney | 424/9.35 |
| 5,714,579 A | 2/1998 | Dean et al. | 530/326 |
| 5,720,934 A | 2/1998 | Dean et al. | 424/1.69 |
| 5,770,179 A | 6/1998 | Dean | 424/1.73 |
| 5,849,261 A | 12/1998 | Dean et al. | 424/1.69 |
| 5,922,690 A | 7/1999 | Van Gorp et al. | 514/54 |
| 6,017,511 A | 1/2000 | Wong et al. | 424/1.69 |

FOREIGN PATENT DOCUMENTS

| | | |
|---|---|---|
| CA | 2000650 | 10/1989 |
| DE | 3124384 | 1/1983 |
| EP | 55028 | 6/1982 |
| EP | 554898 | 8/1993 |
| FR | 2584728 | 1/1987 |
| WO | 93/05075 | 3/1993 |

OTHER PUBLICATIONS

Couchman et al (1985), The Journal of Biological Chemistry, vol. 260, No. 25, pp. 13755–13762.*

Kulkarni et al (1995), The Journal of Nuclear Medicine, vol. 36, No. 5, p. 69P, Abstract No. 279.*

Kulkarni et al (1996), Applicantion of Accelerators in Research and Industry, Proceeding of the Fourteenth International Conference, pp. 1341–1344.*

Nagasawa et al, "Chemical Sulfation of Preparations of Chondroitin 4– and 6–Sulfate, and Dermatan Sulfate Preparation of Chondroitin Sulfate E–Like Materials From Chondroitin," *Carbohydrate Research*, 158, No. 1 (Dec. 1986), pp. 183–190, Amsterdam, Netherlands.

Linhardt et al, "Dermatan Sulfate as a Potential Therapeutic Agent," *Gen. Pharmar.*, 26, No. 3 (1995), pp. 443–451.

Volpi et al, "Physico–Chemical Properties and the Structure of Dermatan Sulfate Fractions Purified from Plasma after Oral Administration in Healthy Human Volunteers," *Thromb. Haemostas.*, 75 (1996), pp. 491–496.

Moyer et al, "Technetium–99m–White Blood Cell–Specific Imaging Agen Developed from Platelet Factor 4 to Detect Infection," *J. Nuclear Med*, 37, No. 4 (1996), pp. 673–679.

Brister et al, "Is Heparin the Ideal Anticoagulant for Cardiopulmonary Bypass? Dermatan Sulphate May be an Alternative," *Thromb. Haemostas.*, 71 (1994), pp. 468–473.

Linhardt et al, "Low Molecular Weight Dermatan Sulfate as an Antithrombotic Agent," *Biochem. Pharm.*, 47, No. 7 (1994), pp. 1241–1252.

Pollack et al, "Imaging Inflammation with $^{99}$Tc$^m$–Labelled Chemotactic Peptides: Analogues with Reduced Neutropenia," *Nuclear Med. Comm.*, 17 (1996), pp. 132–139.

Maimone et al, "Structure of a Dermatan Sulfate Hexasaccharide that Binds to Heparin Cofactor II with High Affinity," *J. Biol. Chem.*, 265, (1990), pp. 1863–18271.

Ferrari et al, "Preliminary Chemical, Biochemical, and Pharmacological Characterization of a Low Molecular Weight Dermatan Sulphate," *Carbohydrate Res.*, 255, No. 3 (1994), pp. 125–132.

Mascellani et al, "Quantitation of Dermatan Sulfate Active Site for Heparin Cofactor II by $^1$H Nuclear Magnetic Resonance Spectroscopy," *Anal. Biochem..*, 223 (1994), pp. 135–141.

(List continued on next page.)

Primary Examiner—Dameron Jones
(74) Attorney, Agent, or Firm—Eric W. Guttag; Smith, Guttag, Hasse & Nesbitt

(57) ABSTRACT

A selectively targeted agent comprising a dermatan sulfate having more than about 25% repeating L-iduronic acid→4, 6-di-O-sulfated N-acetyl-D-galactosamine disaccharide units that is covalently attached or bonded to a radioactive metal-ion binding moiety. The targeted agent is useful in preparing radiagnostic and/or radiopharmaceutical agents for diagnostic and/or therapeutic treatment when combined with an appropriate radioactive metal ion such as $^{99m}$Tc, $^{186}$Re or $^{188}$Re.

20 Claims, No Drawings

OTHER PUBLICATIONS

Pavao et al, "A Unique Dermatan Sulfate–Like Glycosaminoglycan from Ascdian," *J. Biol. Chem.,* 270, No. 52 (Dec. 29, 1995), pp. 31027–31036.

Volpi et al, "Dermatan Sulfate from Beef Mucosa: Structure, Physiochemical and Biological Properties of Fractions Prepared by Chemical Depolymerization and Anion–Exchange Chromatography," *Carbohydrate Res.,* 255, (1994), pp. 133–144.

Agnelli, "New Antithrombins and Nonheparin Glycosaminoglycans in Clinical Development," *Vessels,* 1 (1995), pp. 9–16.

Bergonzini et al, "Pharmacokineics of Native and Low Molecular Weight Dermatans: Preliminary Studies in Rats and Primates," *Seminars in Thrombosis and Hemostasis, Sup* 2, (1990), pp. 235–239.

Dunstone et al, "Ion–Exchange Reactions Between Acid Mucopolysaccharides and Various Cations," *Biochem.J.,* 85, No. 3 (1962), pp. 336–351.

Fareed et al, "Molecular and Functional Heterogeneity in Dermatan Sulfate Preparations," *Seminars in Thrombosis and Hemostasis,* 17, supp 2 (1991), pp. 174–180.

Maaroufi et al, "Influence of the Oversulfation Method and the Degree of Sulfation on the Anticoagulant Properties of Dermatan Sulfate Derivatives," *Thromb. Res.,* 59, (1990), pp. 749–758.

Mascellani et al, "Relative Influence of Different Disulphate Disaccharide Clusters on the HCII–Mediated Inhibition of Thrombin by Dermatan Sulfates of Different Origins," *Thromb. Res.,* 74, (1994), pp. 605–615.

Matthiasson et al, "The Haemorrhagic Effect of Low Molecular Weight Heparins, Dermatan Sulphate and Hirudin," *Haemostasis,* 25 (1995), pp. 203–211.

Ofosu et al, "Increased Sulphation Improves the Anticoagulant Acitivities of Heparan Sulphate and Dermatan Sulphate," *Biochem. J.,* 248, (1987), pp. 889–896.

Ofosu et al, "Heparan Sulfate and Dermatan Sulfate Inhibit the Generation of Thrombin Activity in Plasma by Complementary Pathways," *Blood,* 64, No. 3 (1984), pp. 742–747.

Thomas et al, "Relative Efficacy of Heparin and Related Glycosaminoglycans as Antithrombotic Drugs," *Ann. N.Y. Acad. Sci.,* 556 (1989), pp. 313–322.

Tollefsen et al, "The Interaction of Glycosaminoglycans with Heparin Cofactor II: Structure and Activity of a High–Affinity Dermatan Sulfate Hexasaccharide," *Plenum Press,* (1992), pp. 167–176.

Tollefsen et al, Heparin Cofactor II. Purification and Properties of a Heparin–Dependent Inhibitor of Thrombin in Human Plasma, *J. Biol. Chem.,* 257, (1982), pp. 2162–2169.

Okwusidi et al, "In Vivo Catalysis of Thrombin Inhibition by Antithrombin III or Heparin Co–Factor II and Antithrombotic Effect: Differential Effects of Unfractioned Heparin and Dermatan Sulfate," *Thromb. Haeorrh. Disorders,* 1, (1990), pp. 77–80.

Whinna et al, "Interaction of Heparin Cofactor II with Biglycan and Decorin," *J. Biol. Chem.,* 268, (1993), pp. 3920–3924.

Van Ryn–McKenna, "Dermatan Sulfate: A New Concept in Antithrombotic Therapy," *Diss. Abstr. Int.,* B 53, (1993), pp. 5662.

Ryan et al, "Antithrombotic Properties of Dermatan Sulfate (MF701) in Haemodialysis for Chronic Renal Failure," *Thromb. Haemostas.,* 68 (1992), pp. 563–569.

Fernandez et al, "Catalysis of Thrombin Inhibition Provides an Inde for Estimating the Antithrombotic Potential of Glycosaminoglycans in Rabbis," *Thromb. Haemostas.,* (1987), pp. 286–293.

Fernandez et al, "The Hemorrhagic and Antithrombotic Effects of Dermatan Sulfate," *Brit. J. Haematol.,* 64 (1986), pp. 309–317.

Coons, "Monoclonal Antibodies: The Promise and the Reality," *Radiol. Technol.* (1995) 88, pp. 39–64.

Kulkarni et al, "Novel Glycosaminoglycans (GLYCOS) for Rapid Tumor Delivery of Radionuclides by Selective Binding to Neovascular Endothelium: Potential Agents for Tumor Imaging and Therapy," *Soc. Nucl. Med.* (1995), 36, p. 69P.

Sakahara et al, "Anti–Murine Antibody Response to Mouse Monoclonal Antibodeis in Cancer Patients," *Jpn. J. Cancer Res.* (1997), 88, pp. 895–899.

Farah et al, "The Development of Monoclonal Antibodies for Cancer Therapy," *Crit. Rev. Eukaryot. Gene Expr.* (1998) 88, pp. 321–356.

Kulkarni et al, "Tumor Imaging with Novel Radiogallium (67/68Ga) Labeled Agents," *Application Accelerators in Research and Industry* (1996), pp. 1341–1344.

Ofosu et al, "Thrombin–Catalyzed Amplification and Inhibitory Reactions of Blood Coagulation. In Thrombin: Its Key Role in Thrombogenesis–Implications for its Inhibition Clinically," *CRC Press* (1995) pp. 1–18.

Fenton et al, "Thrombin and Antithrombotics," *Semin. Thromb. Hemostas.* (1998) 24, pp. 87–91.

Naschitz et al, "Diagnosis of Cancer–Associated Vascular Disorders," *Cancer* (1996) 152, pp. 1759–1767.

Haralabopoulos et al, "Thrombin Promotes Endothelial Cell Alignment in Matrigel In Vitro and Angiogenesis In Vivo," *Am. J. Physiol.* (1997) 273, pp. C239–245.

Folkman, et al "Blood Vessel Formation: What Is its Molecular Basis?, " *Cell* (1996) 87, pp. 1153–1155.

Folkman et al, "Fighting Cancer by Attacking its Blood Supply," *Sci. Am.* (1996) 275, pp. 150–154.

Folkman et al, "Addressing Tumor Blood Vessels," *Nat. Biotechnol.* (1997) 15, p. 510.

Folkman et al, "Tumor Angiogenesis and Tissue Factor," *Nat. Med.* (1996) 275, pp. 167–168.

Pinedo et al , "Involvement of Platelets in Tumor Angiogenesis?" *Lancet* (1998) 352, pp. 1775–1777.

Inufusa et al, "Correlation of Prognosis of Breast Cancer Patients and Expression of Ley which Acts as a Cofactor of Tumor Procoagulant," *Int. J. Oncol.* (1998) 13, pp. 481–487.

Shoji et al, "Activation of Coagulation and Angiogenesis in Cancer: Immunohistochemical Localization In Situ of Clotting Proteins and Vascular Endothelial Growth Factor in Human Cancer," *Am. J. Pathol.* (1998) 152, pp. 399–411.

Donati et al, "Cancer Procoagulant in Human Tumor Cells: Evidence from Melanoma Patients," *Cancer Res.* (1986) 46, pp. 6471–6474.

Furie et al., "Molecular and Cellular Biology of Blood Coagulation," *N. Eng. J. Med.* (1992) 326, pp. 800–806.

Hsieh, "Thrombin Interaction with Fibrin Polymerizing Sites," *Thromb. Res.* (1997) 86, pp. 301–316.

Gordon et al, "Cancer Cell Procoagulants and their Role in Malignant Disease," *Semin. Thromb. Hemost.* (1992) 2, pp. 424–433.

Tsubura et al, "Inhibition of the Arrest of Hematogenously Disseminated Tumor Cells," *Cancer Metastases Rev.* (1983) 2, pp. 223–237.

Kumar et al, "The Influence of Fibrinogen and Fibrin on Thrombin Generation–Evidence for Feedback Activation of the Clotting System by Clot Bound Heparin," *Thromb. Hemost.* (1994) 72, pp. 713–721.

Liu et al, "The Binding of Thrombin to Fibrin," *J. Biol. Chem.* (1979) 254, pp. 10421–10425.

Buchanan et al, "Evidence for a Conformational Change of Surface–Bound Thrombin that Promotes Vessel Wall Thrombogenecity: Selective and Sustained Inhibition of its Activity by Intimatan but not by Heparin," *Thromb. Haemost.* (1999) ISTH Suppl., p. 413.

Weitz et al, "Clot–Bound Thrombin Is Protected from Inhibition by Heparin–Antithrombin III but Is Susceptible to Inactivation by Antithrombin III–Independent Inhibitors," *J. Clin. Invest.* (1990) 86, pp. 385–391.

Buchanan et al, "A Rationale for Targeting Antithrombotic Therapy at the Vessel Wall: Improved Antithrombotic Effect and Decreased Risk of Bleeding," *Wien Klin Wochenschr* (1999) 111, pp. 81–89.

Brister et al, "Effect of Heparin and CL–0313 on Complement Activation In Vitro and Thrombin Generation During Cardiopulmonary Bypass In Vivo," *Haemostasis* (1996) 26, pp. 575.

Zucker et al, Vascular Endothelial Growth Factor Induces Tissue Factor and Matrix Metalloproteinase Production in Endothilial Cells: Conversion of Prothrombin to Thrombin Results in Progelatinase A Activation and Cell Proliferation, *Int J. Cancer* (1998) 75, pp. 780–786.

Duhamel–Clerin et al, "Thrombin Receptor–Mediated Increase in Two Matrix Metalloproteinases MMP–1 and MMP–3, in Human Endothelial Cells," *Arteriscler. Thromb. Vasc. Biol.* (1997) 75, pp. 1931–1938.

Senger et al, "Stimulation of Endothelial Cell Migration by Vascular Permeability Factor/Vascular Endothelial Growth Factor Through Cooperative Mechanisms Involving the Alpha v. Beta–3 Integrin, Osteoponitn, and Thrombin," *Am. J. Pathol.* (1996) 75, pp. 293–304.

Smith et al., "Platelet Responses to Compound Interactions with Thrombin" *Biochemistry* (1999) 38, pp. 8936–8947.

Kasirer–Friede et al., "Thrombin receptor occupancy modulates aggregation efficiency and platelet surface expression of vWF and thrombosopodin at low thrombin concentrations" (1999) *Thromb. Haemost.* 81, pp. 967–975.

Liu et al, "New Approaches for the Preparation of Hydrophobic Heparin Derivatives," *J. Pharm. Sci.* (1994) 83, pp. 1034–1039.

Ruci'nska et al, "Activity of Cancer Procoagulant (CP) in Serum of Patients with Cancer of Lung, Breast, Oesophagus and Colorectum," *Acta Biochim. Pol.* (1997) 44, pp. 109–112.

Gordon et al, "Cancer Procoagulant: A Factor X Activator, Tumor Marker and Growth Factor from Malignant Tissue," *Blood Coagul. Fibrinolysis* (1997) 92, pp. 73–36.

Gianese et al, "The Pharmacokinetics and Pharmacodynamics of Dermatan Sulfate MF701 During Haemodialysis for Chronic Renal Failure," *Brit. J. Clin. Pharm.* (1993) 35, pp. 335–339.

Nurmohamed et al, "Clinical Experience with a New Antithrombotic (Dermatan Sulfate) in chronic Hemodialysis Patients," *Clin. Neph.* (1993) 39, pp. 166–171.

Cofranesco et al, "Dermatan Sulfate for the Treatment of Disseminated Intravascular Coagulation (DIC) in Acute Leukemia: A Randomized, Heparin–Controlled Pilot Study," *Thrombosis Res.* (1994) 74, pp. 65–75.

Cohen et al, "A Dose Ranging Study to Evaluate Dermatan Sulfate in Preventing Deep Vein Thrombosis Following Total Hip Arthroplasty," *Thromb. Haemost.* (1994) 72, pp. 793–798.

Musanti et al, "In Vitro Inhibition of Rat Arterial Smooth Muscle Cell Growth by Extractive Sulfated Mucopolysaccharides," Pharm. Res. Comm (1985), 17, No. 1, pp. 69–84.

Kiss, "β–Eliminative Degradation of Carbohydrates Containing Uronic Acids Residues," *Adv. Carbohydr. Chem. Biochem.* , 29 (1974), pp. 229–303.

Linhardt, "Structural Features of Dermatan Sulfates and Their Relationship to Anticoagulant and Antithrombotic Activities," *Biochem. Pharm.* (1991) 42, No. 8, pp. 1609–1619.

Mascellani et al, "Active Site for Heparin Cofactor II in Low Molecular Mass Dermatan Sulfate. Contribution to the Antithrombotic Activity of Fractions with High Affinity for Heparin Cofactor II," *Thromb. Res.* (1996) 84, No. 1, pp. 21–32.

Murata et al, "Occurrence of an Oversulfated Dermatan Sulfate in Kidney Tissue," Renal Physiol. (1978) 1, No. 1, pp. 48–55.

* cited by examiner

TARGETED AGENTS USEFUL FOR DIAGNOSTIC AND THERAPEUTIC APPLICATIONS

CROSS-REFERENCE TO RELATED APPLICATION

This application claims the benefit of copending U.S. Provisional Patent Application Ser. No. 60/128,139, filed Apr. 7, 1999.

TECHNICAL FIELD

The present application relates to agents useful in diagnostic applications for detecting vascular injury, disease, disorders and/or neovascularization processes, as well as in therapeutic applications for treating certain such disease states, especially those that are associated with the activation of thrombin. In particular, the present application relates to selectively targeted agents useful in preparing diagnostic and/or therapeutic agents, especially those that have greater affinity for thrombin.

BACKGROUND OF THE INVENTION

Monoclonal antibody- and peptide-metal ion chelates have been used in variety of diagnostic and therapeutic applications. For instance, when directed to tumor-specific antigens, monoclonal antibodies have been used as carriers of covalently chelated radioactive metal ions in radioimaging and radiopharnaceutical applications. However, the utility of monoclonal antibody carriers as radioimaging agents is limited by bioavailability, biodistribution, metabolism and excretion problems in terms of loading tumor sites relative to background tissues and bodily fluids because they require long equilibration times to achieve suitable contrast for medical imaging purposes. See Sakahara et al, "Monoclonal Antibodies: The Promise and the Reality," Radiol. Technol. (1995) 88: 39–64. Although highly specific for a given tumor antigen, i.e. not associated with normal tissues, the utility of these antibody carriers as medically suitable radiodiagnostic and radio-therapeutic agents is further limited due to clonal heterogeneity of expressed tumor antigens. See Sakahara et al, "Status of Radiolabeled Monoclonal Antibodies for Diagnosis and Therapy of Cancer," Oncology (1996) 88: 939–953. Such antibody conjugates also suffer from host immune reactions such as the HAMA response, serum sickness and bone marrow toxicity that severely limit their effectiveness. See Sakahara et al, "Anti-Murine Antibody Response to Mouse Monoclonal Antibodies in Cancer Patients," Jpn. J. Cancer Res. (1997) 88: 895–899. CDR grafting techniques, bispecific and single chain antibody designs have been invoked to minimize anti-antibody reactions, but such reagents are difficult and expensive to manufacture. See Sakahara et al, "The Development of Monoclonal Antibodies for Cancer Therapy," Crit. Rev. Eukaryot. Gene Expr. (1998) 88: 321–356. Others which target fibrin-specific antigens typical of venous thrombi are limited in that they may not adequately image platelet-rich thrombi associated with the arterial circulation. Moreover, antibodies to platelet-specific antigens are useful to image such thrombi but may not adequately detect those associated with venous events.

A variety of synthetic peptides chelated to radioactive nuclides with high affinity for tumor-associated receptors have also been described which exhibit biodistribution, metabolism and excretion properties more favorable than antibody-mediated carriers and with more rapid localization to tumors. See Raderer et al, "Regulatory Peptide Receptors as Molecular Targets for Cancer Diagnosis and Therapy," Q. J. Nucl. Med. (1998) 39: 63–70. Although having improved utility relative to monoclonal antibodies, chelates of the peptide carriers in certain, limited instances, suffer in that they too are limited in utility by heterogeneity of expressed tumor antigens and are mostly limited to tumors of neuroendocrine origin that preferentially express neuroendocrine receptors such as somatostatin, VIP or bombesin-like receptors in a tissue-specific manner and thus are not useful for detecting and treating tumors of non-neuroendocrine origin. Thus, the same issues of receptor heterogeneity and tissue-specific expression of tumor antigens that restrict the utility of antibody approaches are also inherent to peptide-based targeting approaches for diagnosis and treatment applications. See Sakahara et al, "Status of Radiolabeled Monoclonal Antibodies for Diagnosis and Therapy of Cancer," Oncology (1996) 88: 939–953. Target expression is also a critical issue with peptide approaches for the detection of thrombo-embolic diseases. Peptide chelates to GPIIb/IIIa integrin receptors based on the RGDS target sequence, for example, are highly useful in the detection and imaging of platelet-rich thrombi, but like the antibody approaches that also target platelet-specific antigens, such peptide chelates are not widely applicable to all thrombotic disease states. Such peptide chelates suffer the further disadvantage that a different peptide sequence and structure optimization program must be invoked for each different target receptor, i.e., each targeted receptor or epeitope requires a unique peptide-binding structure. The development of a diagnostic peptide-chelate, or therapeutic peptide-chelate, must undergo a unique preclinical program involving toxicology for each peptide to each receptor targeted as well as a tailored chemistry optimization program to analog around a variety of structures which then must be individually evaluated in in vitro and in vivo assays to identify the best peptide in terms of potency, receptor affinity, receptor selectivity, in vivo stability against proteolytic degradation, targeting, biodistribution, metabolism, safety, efficacy, ease of synthesis, as well as cost of manufacture considerations. Again, a key aspect to the development of peptide (or antibody)based targeting agents for detecting sites of disease or delivering a therapeutic radiopharmaceutical to such sites are useful only when the specific antigen or receptor being targeted is expressed at the disease site. Such receptors must be first validated and thus proven to have a preferential disease association that ultimately would allow selective targeting that demarcates diseased from normal tissues. Thus, the utility of a targeting agent is only as valid as the receptor or antigen that it targets in the context of its association to a given disease state. For example, clonal heterogeneity of tumor cell antigen expression may result in the efficient ablation of the receptor-expressing populations by peptide or antibody radiotherapeutic conjugates, thus allowing for the selection and clonal expansion of the non-receptor expressing populations that are now refractory to such further treatments or detection.

Thrombin, on the other hand, is a highly validated disease target associated with a wide breadth of disease states. See Ofosu et al, "Thrombin-Catalyzed Amplification and Inhibitory Reactions of Blood Coagulation. In Thrombin: Its Key Role in Thrombogenesis-Implications for its Inhibition Clinically," CRC Press (1995) pp. 1–18; Fenton et al, "Thrombin and Antithrombotics," Semin. Thromb. Hemostas. (1998) 24: 87–91. The ability to detect and diagnose diseased and/or rejuvenating endothelium associated with vascular injury, disease and/or neovascularization processes is important. It is particularly desirable to be able to diagnose indications of disease where a vascular pathology associated with enhanced thrombogenicity is involved. By way of limited example, such disease states having an active thrombin component include a variety of thrombo-occlusive disorders, such as infarction, stroke, restenosis associated with percutaneous transluminal coronary angioplasty, coronary artery diseases such as atherosclerosis, peripheral vascular disease and cerebral vascular disease, as well as venous occlusive disorders such as deep vein thrombosis, and a variety of malignancies involving hypercoagulopathies and vascularized tumor networks. Thrombo-occlusive disorders of the circulatory system may also arise as a result of surgical procedures. Certain vasculopathies can be an early indicator of occult malignancy even before signs and symptoms of the tumor itself become obvious. See Naschitz, et al, "Diagnosis of Cancer-Associated Vascular Disorders," *Cancer* (1996) 152: 1759–1767. Thus, an agent that can target the cancer associated with such vascular disorders can be extremely valuable for the diagnosis and treatment of hidden cancers. For example, it is well known that thrombin becomes activated in response to vessel injury due to trauma or disease and moreover, is associated with neovascular remodeling processes associated with new blood vessel formation, a process referred to as angiogenesis. See, for example Haralabopoulos et al, "Thrombin Promotes Endothelial Cell Alignment in Matrigel In Vitro and Angiogenesis In Vivo," *Am. J. Physiol.* (1997) 273: C239–245; Folkman, et al "Blood Vessel Formation: What Is its Molecular Basis?," *Cell* (1996) 87: 1153–1155. In particular, tumors induce angiogenesis. See Folkman et al, "Fighting Cancer by Attacking its Blood Supply," *Sci. Am.* (1996) 275: 150–154; Folman, et al, "Addressing Tumor Blood Vessels," *Nat. Biotechnol.* (1997) 15: 510. Tumors become hypoxic at their core and thus exude factors that stimulate new blood vessel growth. This results in the eventual vascularization of the tumor mass so as to provide nutrients for tumor cell growth and a portal by which motile cells invade the circulation and thereby mediate the blood-borne dissemination of cancer. Moreover, a variety of malignancies have associated cancer procoagulant activities involving tissue factor activation, cancer procoagulant enzymes and glycolipid procoagulant cofactors correlating with poor prognosis. See, for example, Folman et al, "Tumor Angiogenesis and Tissue Factor," *Nat. Med.* (1996) 275: 167–168; Pinedo et al , "Involvement of Platelets in Tumor Angiogenesis?" *Lancet* (1998) 352: 1775–1777; Inufusa et al, "Correlation of Prognosis of Breast Cancer Patients and Expression of Ley which Acts as a Cofactor of Tumor Procoagulant," *Int. J. Oncol.* (1998) 13: 481–487. These procoagulant activities process prothrombin yielding an activated thrombin associated in a bound state with tumor cell membranes, endothelium and peri-tumoral tissue components. See, for example, Shoji et al, "Activation of Coagulation and Angiogenesis in Cancer: Immunohistochemical Localization In Situ of Clotting Proteins and Vascular Endothelial Growth Factor in Human Cancer,"*Am. J. Pathol.* (1998) 152: 399–411. Thus, in the tumor vicinity, thrombin becomes associated in a bound state not only with the vascular wall of the tumor's blood vessel network but also with the tumor and surrounding tissues. The procoagulant activity of colonizing cells recruit prothrombin from the fluid-phase, stimulate its activation on the tumor cell surface to yield surface-bound thrombin which consumes soluble fibrinogen to form a coat of fibrin that covers the surface of invading cells during the circulatory phase of the metatstatic process. See, for example, Donati et al, "Cancer Procoagulant in Human Tumor Cells: Evidence from Melanoma Patients," *Cancer Res.* (1986)46: 6471–6474.

Fibrin is the insoluble form of fibrinogen that results from the specific action of activated thrombin on the fibrinogen chain. See Furie et al., "Molecular and Cellular Biology of Blood Coagulation," *N. Eng. J. Med.* (1992) 326: 800–806; Hsieh, "Thrombin Interaction with Fibrin Polymerizing Sites," *Thromb. Res.* (1997) 86: 301–316. Fibrin, formed on the procoagulant tumor cell surface, is a self-antigen that is not recognized by the host immune system. Thus, it forms a cloaking device by which invading tumor cells escape immune surveillance during the circulatory phase of the metastatic cascade. See Gordon et al, "Cancer Cell Procoagulants and their Role in Malignant Disease," *Semin. Thromb. Hemost.* (1992) 2: 424–433. These invading cell clones form aggregates or emboli which are further capable of activating platelets via activated thrombin bound to surface-deposited fibrin and thus form an adhesive cellular mesh of tumor cells, fibrin and bound thrombin which lodge in the capillary venules of target organs. See Tsubura et al, "Inhibition of the Arrest of Hematogenously Disseminated Tumor Cells," *Cancer Metastases Rev.* (1983) 2: 223–237. Tumor cells associated with such emboli then extravasate the circulation, invade and colonize target tissues. These newly established tumor colonies eventually grow and vascularize. Thrombin, however, is found tightly bound to fibrin and is also associated with the platelet surface via specific thrombin receptors. See Kumar et al, "The Influence of Fibrinogen and Fibrin on Thrombin Generation-Evidence for Feedback Activation of the Clotting System by Clot Bound Heparin," *Thromb. Hemost.* (1994) 72: 713–721; Liu et al, "The Binding of Thrombin to Fibrin," *J. Biol. Chem.* (1979) 254: 10421–10425; Smith at al., "Platelet Responses to Compound Interactions with Thrombin" *Biochemistry* (1999) 38: 8936–8947; Kasirer-Friede et al, "Thrombin Receptor Occupancy Modulates Aggregation Efficiency and Platelet Surface Expression of vWF and Thrombospondin at Low Thrombin Concentrations" (1999) *Thromb. Haemost.* 81: 967–975. Thrombin is also a self antigen. Thus, whereas such emboli comprised of thrombin, fibrin and platelets are not readily susceptible to detection by the host immune system, the bound thrombin associated with the emboli is susceptible to detection by the activation of the natural serine protease inhibitor, heparin cofactor II, that is endogenous to the host. Heparin cofactor II has high selectivity for thrombin in its surface-associated or bound state. See, for example, Buchanan et al, "Evidence for a Conformational Change of Surface-Bound Thrombin that Promotes Vessel Wall Thrombogenecity: Selective and Sustained Inhibition of its Activity by Intimatan but not by Heparin," *Thromb. Haemost.* (1999) ISTH Suppl.:413; Weitz et al, "Clot-Bound Thrombin Is Protected from Inhibition by Heparin-Antithrombin III but Is Susceptible to Inactivation by Antithrombin III-Independent Inhibitors," *J. Clin. Invest.* (1990) 86: 385–391; Buchanan et al, "A Rationale for Targeting Antithrombotic Therapy at the Vessel Wall: Improved Antithrombotic Effect and Decreased Risk of Bleeding," *Wien Klin Wochenschr* (1999) 111: 81–89; Brister et al, "Effect of Heparin and CL-0313 on Complement Activation In Vitro and Thrombin Generation During Cardiopulmonary Bypass In Vivo," *Haemostasis* (1996) 26: 575. Heparin cofactor II is ubiquitously distributed and is present in the systemic circulation and in the extravascular tissues. Thus, its biodistribution within the mammalian body is suitable to bind and neutralize thrombin in remote body residua potentially associated with occult disease states including infection and malignancies as well as the more accessible circulatory sites confined to the vascular compartments so associated with the venous and arterial thrombo-occlusive disorders.

Others have suggested using various glycosaminoglycans (GAGs) in combination with radioactive metal-ion chelates, alone or in combination with specific receptor-targeting peptides. For example, U.S. Pat. 5,561,201 (Dean et al), issued Oct. 1, 1996 and U.S. Pat. No. 5,714,579 (Dean et al), issued Feb. 3, 1998, disclose a radiolabeled imaging reagent composition comprised of a polybasic compound covalently linked to technetium-99 m binding moiety that is admixed with a polysulfated glycan, such as heparin, heparin sulfate, chondroitin sulfate or dermatan sulfate, and the composition being capable of binding to inflammation sites in vivo. See also U.S. Pat. No. 5,770,179 (Dean), issued Jun. 23, 1998, which discloses β-glucans radiolabeled with technetium-99 m for diagnostic imaging where the imaging is mediated by the binding of the radiolabeled β-glucan to β-glucan receptors on monocytes, macrophages and neutrophils and thus relies on a cell-mediated inflammatory component associated with disease.

Another example is U.S. Pat. No. 5,707,606 (Ranney), issued Jan. 13, 1998, which discloses diagnostic agents comprised of a GAG, such as dermatan sulfate, essentially purified dermatan sulfate with a sulfur content of up to 9% and with selective oligosaccharide oversulfation, chondroitin sulfate, oversulfated chondroitin sulfate, and heparin sulfate, in non-covalent (ionic) and covalent combination with cationic, electrophilic metal-ion chelates that are alleged to improve the site delivery, uptake mechanism, sensitivity and kinetic-spatial profiles of the metal-ion chelate by directing the metal-ion chelate to sites of vascular inflammation.

There still remains a need for radiolabeled and radioactive diagnostic and therapeutic agents that are capable of more selectively targeting the site of potential disease or injury for diagnostic or treatment purposes, without the undesired side effects and problems of prior monoclonal antibody agents and synthetic peptides chelated to radioactive metals, and without the complications brought about by ionic formulations of chelates and targeting agents that promote the complex equilibria of self-associating systems in vivo. In particular, it would be desirable to provide radiolabeled and radioactive diagnostic and therapeutic agents and compositions that are capable of detecting vascular injury, disease, disorders and neovascularization processes, as well as treating such disease states, that are associated with the activation of thrombin and especially thrombin bound to disease sites.

SUMMARY OF THE INVENTION

The present invention relates to selectively targeted agents that comprise a dermatan sulfate having more than about 25% repeating L-iduronic acid→4,6-di-O-sulfated N-acetyl-D-galactosamine disaccharide units that is covalently attached or bonded to a radioactive metal-ion binding moiety. The present invention also relates to the use of these targeted agents to prepare radiolabeled and/or radioactive diagnostic and/or therapeutic agents for diagnosing, and/or for treating disease states, disorders and the like. The present invention further relates to methods for diagnosing or treating such disease states which comprises administering a diagnostic and/or therapeutic amount of these selectively targeted radiolabeled and/or radioactive diagnostic and/or therapeutic agents to the person to be diagnosed or treated.

It has been surprisingly discovered that the targeted agents of the present invention are useful in preparing radiolabeled and/or radioactive diagnostic and/or therapeutic agents for the detection of diseased and/or rejuvenating endothelium associated with vascular injury, disease, disorders and/or neovascularization processes having a surface-bound thrombin component and, moreover, are superior and useful in therapeutic applications in the treatment of certain of such disease states having a surface-bound thrombin component. Of particular diagnostic utility are disease indications where the vascular pathology is associated with enhanced thrombogenicity, including but not limited to, thrombo-occlusive disorders involving clot formation, such as infarction, stroke, restenosis associated with percutaneous transluminal coronary angioplasty, coronary artery diseases such as atherosclerosis, peripheral vascular disease and cerebral vascular disease, as well as venous occlusive disorders such as deep vein thrombosis, and, a variety of malignancies involving hypercoagulopathies and vascularized tumor networks. In addition, the targeted radioactive metal ion binding moieties of the present invention are particularly useful in diagnostic and/or therapeutic applications involving the imaging and detection of occult malignancy, as well as the treatment and eradication thereof The targeted agents of the present invention are preferential over prior monoclonal antibody- and peptide targeted agents having an attached metal ion chelate for diagnostic and therapeutic applications. In particular, the dermatan sulfate used in the present invention that is covalently bound or attached to the radioactive metal ion binding moiety is highly optimized in targeting surface-bound thrombin found in association with thrombi and thrombogenic vessels of the circulatory system, associated with a broad array of diverse disease states. The present invention is therefore broadly applicable to diagnostic and therapeutic applications pertaining to these diverse disease states and thus, is not limited by the complicated optimization and manufacturing issues associated with each unique peptide carrier/targeting agent. The targeted agents of the present invention are also advantageous in their lack of metabolism, their targeted biodistribution, and favorable pharmacokinetics and dynamics at diagnostically and therapeutically useful doses. Moreover, at such doses the anticoagulant effects of the targeted agents of the present invention are minimal when used in diagnostic and/or therapeutic applications, causing at most only negligible to mild elevations of activated clotting times (ACT). When used in association with severe disease states such as malignancy, mild ACT elevation is tolerable and moreover, considered beneficial, especially in association with thrombo-occlusive disorders where anticoagulation is a desired effect towards clinical outcome, even when used in diagnostic applications.

The targeted agents of the present invention also do not require cationic chelates or cationic peptides which mediate an association with a glycosaminoglycan (GAG) carrier by charge-charge attractive forces between the positively charged basic amines of the chelated metal ion moiety or peptide, and the negatively charged acidic functionalities of the GAG involving a principal mode of ionic binding. In particular, it has been found according to the present invention that: (1) cationic and electrophilic radioactive metal-ion chelates and cationic radiolabeled peptide-binding moieties are not required to achieve the selective and high-sensitivity detection of diseased tissues; and (2) ionic interactions between acidic mucopolysaccharide and a cationic metal ion chelate, or a cationic, peptide radiolabeled-binding moiety, can be avoided, thus also avoiding the complex issues of metabolism, biodistribution and safety considerations associated with self-associating systems comprising compositions of GAGs in ionic association with metal-binding

DETAILED DESCRIPTION OF THE INVENTION

The targeted agents of the present invention are intended for use with a variety of medically and pharmaceutically acceptable and suitable radioactive metal ions useful in diagnostic and/or therapeutic applications. In diagnostic applications, the radioactive metal ion would be conducive to diagnostic applications (i.e., the radioactive metal ion, when reacted, admixed or otherwise combined with the targeted agent, would form "radiolabeled diagnostic" or "radiodiagnostic" agent), such as, but not limited to, technicium-99 m ($^{99m}$Tc). In therapeutic applications, the radioactive metal ion would have an energy emission engendering an effective killing radius conducive to tumor cell ablation with minimal damage to normal surrounding tissues (i.e., the radioactive metal ion, when reacted, admixed or otherwise combined with the targeted agent, would form "radioactive therapeutic" or "radiopharmaceutical"), such as, but not limited to, for example, rhenium-186 ($^{186}$Re) and rhenium-188 ($^{188}$Re). Some representative radioactive metal ions (radionuclides) useful in the present invention for medical imaging and therapy of pathological sites include, but are not limited to, $^{99m}$Tc, $^{111}$In, $^{67}$Ga, $^{169}$Yb, $^{201}$Tl, $^{153}$Sm, $^{201}$Tl, $^{186}$Re and $^{188}$Re, to name a few. $^{99m}$Tc is preferred for scintigraphic imaging agents currently employed in the medical imaging of disease, as well as emerging diagnostic and/or imaging technologies compatible therewith, as the isotope has a single photon energy of 140 keV and a radiation half-life of ~6h. Other radioactive metal ions and radionuclides, although useful, have longer half-lives which can involve longer patient exposures that may be undesirable. Of particular preference for preparing therapeutic agents according to the present invention are radioactive metal ions such as $^{186}$Re or $^{188}$Re that are used in the medical treatment of vascularized malignancies. Indeed, the targeted agents of the present invention, when used to prepare radiolabeled and radioactive diagnostic and therapeutic agents, are particularly useful in the imaging and detection of occult malignancy, as well as the treatment and eradication thereof The targeted agents comprise a dermatan sulfate (having a particular composition as described hereafter) that is covalently attached or bonded to a radioactive metal-ion binding moiety. Radioactive metal ion binding moieties useful in the present invention can include any of a variety of moieties that are medically and pharmaceutically acceptable, are capable of chelating or complexing with the radioactive metal ions previously described and have a functional group(s) that allow the dermatan sulfate (having a particular composition as described hereafter) to be covalently attached or bound thereto. Radioactive metal ion binding moieties useful in the present invention can be derived from various peptides, boronic acid adducts of dioxime complexes and the like, and preferably have a molecular weight of about 500 to about 1,200 Daltons.

One group of suitable radioactive metal ion binding moieties for use in the present invention include those of formula (I):

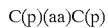
$$C(p)(aa)C(p) \qquad \qquad \text{I.}$$

wherein C is cysteine and (p) is hydrogen or a thiol protecting molecule and (aa) is an amino acid, or a non-amino acid inorganic and/or organic molecule that provides a spacer function between C(p) residues. See U.S. Pat. No. 5,714,579 (Dean et al), issued Feb. 3, 1998, and U.S. Pat. No. 5,849,261 (Dean et al), issued Dec. 15, 1998, both of which are incorporated by reference. Suitable amino acids include glycine, lysine, and alanine. Amino acids that provide an additional reactive amine, such as an ε-amino side chain of lysine, can be used for the purpose of covalent attachment of additional radioactive metal ion binding moieties to increase the number of covalently attached or bound radioactive metal ion binding moieties on a given molecule. The effect and intention of such is to enhance the overall detection sensitivity or therapeutic efficacy of the targeted radioactive metal ion binding moiety when used as a diagnostic or therapeutic agent. The incorporation of multiple targeted radioactive metal ion binding moieties is a concept intended to allow optimization of specific radioactivity of the resulting diagnostic or therapeutic agent so as to vary the dose of ionizing radiation to the target as deemed most efficacious to the particular medical indication being diagnosed and/or treated. Varying the number of covalently attached radioactive metal ion binding moieties is henceforth referred to as valency. For monovalently coordinated radioactive metal ion binding moieties of the present invention, glycine is a preferred amino acid. In another preferred embodiment, the radiolabeled binding moiety of formula (I) can be represented in a covalently concatenated form, i.e. in tandem as a repeated linear sequence of [C(p)(aa)C(p)]n, where n≧2 to increase the number of radiolabeled binding moieties that are attached covalently to the targeted agent, thus increasing valency and where (aa) is an amino acid, or a non-amino acid inorganic and/or organic molecule that provides a spacer function between the C(p) residues defined above. Suitable amino acids include glycine, lysine, and alanine. In another preferred embodiment, however, (aa) can be a saturated aliphatic spacer comprising from about one to ten, and more preferably from about one to five carbon atoms and including a nitrogen atom to aid metal ion coordination and where n≧1. The spacer is designed and intended to provide the optimal geometry and chemical environment for optimal coordination and retention of the radioactive metal ion or nuclide when reacted, admixed or otherwise combined with the targeted agents of the present invention. Furthermore, it is realized by those skilled in the art of organic and inorganic synthesis, as well as medicinal chemistry, that such spacers can comprise a variety of organic and inorganic chemical variations, by way of example, but not limited to, those consisting of heteroatoms, aromatic and non-aromatic heterocyclics, wherein such spacers can impose conformationally constrained geometries for the purpose of enhancement of metal-ion binding and retention by the radioactive metal ion binding moiety or imposing preferred medicinal properties relating to improved physical-chemical and physiological attributes of the imaging and/or radiotherapeutic agents prepared from such targeted agents.

Another group of suitable radioactive metal ion binding moieties for use in the present invention include those of formula (II):

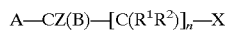
$$A\text{—}CZ(B)\text{—}[C(R^1R^2)]_n\text{—}X \qquad \qquad \text{II.}$$

wherein A is H, HOOC, H$_2$NOC, (dermatan sulfate)-(linker)—NHOC, (dermatan sulfate)-(linker)—OOC or R$^4$, B is H, SH or —NHR$^3$, —N (R$^3$)-(linker)-(dermatan sulfate) or R$^4$; X is SH or —NHR$^3$, —N (R$^3$)-(linker)-(dermatan sulfate) or R$^4$; R$^1$, R$^2$, R3 and R$^4$ are independently H or straight or branched chain or cyclic or cyclic lower alkyl; n is 0, 1, 2; and (1) where B is —NHR$^3$ or —N (R$^3$)-(linker)-

(dermatan sulfate), X is SH and n is 1 or 2; (2) where X is —NHR³ or —N (R³)-(linker)-(dermatan sulfate), B is SH and n is 1 or 2; (3) where B is H or R⁴, A is HOOC, H₂NOC, (dermatan sulfate)-(linker)—NHOC or (dermatan sulfate)-(linker)—OOC, X is SH and n is 0 or 1; (4) where A is H or R⁴, then where B is SH, X is —NHR³ or —N(R)³-(linker)-(dermatan sulfate) and where X is SH, B is —NHR³ or —N(R³)-(linker)-(dermatan sulfate); (5) where X is H or R⁴, A is HOOC, H₂NOC, (dermatan sulfate)-(linker)—NHOC or (dermatan sulfate)-(linker)—OOC and B is SH; (6) where Z is methyl, X is methyl, A is HOOC, H₂NOC, (dermatan sulfate)-(linker)—NHOC or (dermatan sulfate)-(linker)—OOC and B is SH and n is 0; and (7) where Z is SH and X is SH , n is not 0; and wherein the thiol moiety is in the reduced form. See U.S. Pat. No. 5,714,579 (Dean et al), issued Feb. 3, 1998, and U.S. Pat. No. 5,849,261 (Dean et al), issued Dec. 15, 1998, both of which are incorporated by reference.

Another group of suitable radioactive metal ion binding moieties for use in the present invention (when bound to dermatan sulfate) include those of formulas (III or IV):

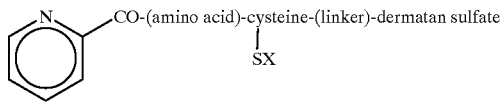

or,

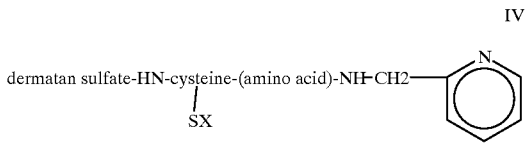

See U.S. Pat. No. 5,714,579 (Dean et al), issued Feb. 3, 1998, and U.S. Pat. No. 5,849,261 (Dean et al), issued Dec. 15, 1998, both of which are incorporated by reference. For purposes of the present invention, X is H or a protecting group; (amino acid) is any amino acid, including amino acids that may be employed to provide an additional reactive amine, such as an ε-amino side chain of lysine, for the purpose of increasing valency. For monovalently coordinated radiolabeled agents and compositions of the present invention, glycine is a preferred amino acid and X is an acetamidomethyl protecting group.

Another group of suitable radioactive metal ion binding moieties for use in the present invention include bisamino bisthiol radioactive metal ion binding moieties. See U.S. Pat. No. 5,714,579 (Dean et al), issued Feb. 3, 1998, and U.S. Pat. No. 5,849,261 (Dean et al), issued Dec. 15, 1998, both of which are incorporated by reference. The bisamino bisthiol radiolabeled-binding moieties are selected from the group consisting of those having formulas (V or VI):

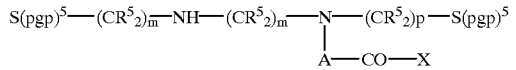

wherein each R⁵ can be independently H, CH₃ or C₂H₅; each (pgp)⁵ an be independently a thiol protecting group or H; m, n, and p are independently 2 or 3; A is a linear or cyclic lower alkyl, aryl, heterocyclyl, combinations or substituted derivatives thereof; and X is (linker)-dermatan sulfate; or

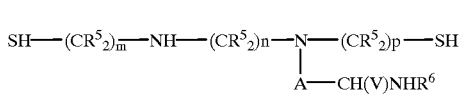

wherein each R⁵ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or —CO-(linker)-dermatan sulfate; R⁶ is H or a (linker)-dermatan sulfate; provided that when V is H, R⁶ is a (linker)-dermatan sulfate and when R⁶ is H, V is a —CO-(linker)-dermatan sulfate.

Another group of suitable radioactive metal ion binding moieties for use in the present invention include those of formula (VII):

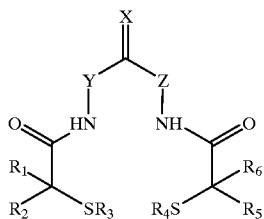

wherein R₁, R₂, R₅ and R₆ are independently selected from H, carboxyl, lower alkyl, and lower alkyl substituted with a group selected from hydroxyl, sulfhydryl, halogen, carboxyl and aminocarbonyl, or a conjugating group; R₃ and R₄ are independently selected from H or a sulfur protecting group; X is selected from 0, the group NH₂⁺, or the group CH₂ each of which may have attached thereto a conjugating group; Y and Z are independently selected from the group CR₁R₂ or NR₇; and R₇ is selected from H, carboxyl, lower alkyl and lower alkyl substituted with hydroxyl, carboxyl and halogen. See U.S. Pat. No. 5,574,140 (Pollack et al), issued Nov. 12, 1996, which is incorporated by reference.

Another group of suitable radioactive metal ion binding moieties for use in the present invention include those of formula (VIII):

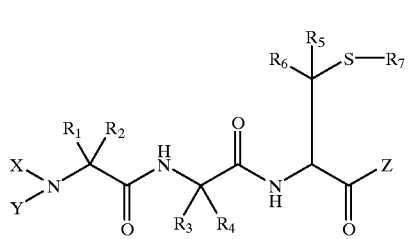

wherein X is a linear or branched, saturated or unsaturated C₁₋₄ alkyl chain that is optionally interrupted by one or two heteroatoms selected from N, O and S; and is optionally substituted by one or more substituents selected from halogen, hydroxyl, amino, carboxyl, C₁₋₄ alkyl, aryl and C(O)Z; Y is H or a substituent defined by X; X and Y may together form a 5- to 8-membered saturated or unsaturated heterocyclic ring optionally substituted by one or more substituents selected from halogen, hydroxyl, amino, carboxyl, oxo, $C_{1-4}$ alkyl, aryl and C(O)Z; $R_1$ through $R_4$ are selected independently from H; carboxyl; $C_{1-4}$ alkyl, $C_{1-4}$ alkyl substituted with a substituent selected from hydroxyl, amino, sulfhydryl, halogen, carboxyl, $C_{1-4}$ alkoxycarbonyl and aminocarbonyl; an alpha carbon side chain of a D- or L-amino acid other than proline; and C(O)Z; $R_5$ and $R_6$ are selected independently from H; carboxyl; amino; $C_{1-4}$ alkyl; $C_{1-4}$ alkyl substituted by a substituent selected from hydroxyl, carboxyl and amino; and C(O)Z; $R_7$ is selected from H and a sulfur protecting group; and Z is selected from hydroxyl, alkoxy, an amino acid residue, and a linking group. See U.S. Pat. No. 6,017,511 (Wong et al), issued Jan. 25, 2000, which is incorporated by reference Another group of suitable radioactive metal ion binding moieties for use in the present invention include those of formula (IX):

wherein X is an anion, Y is a vicinal dioxime of formula (X):

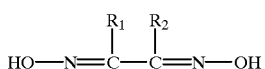

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are —$(C\ R_8\ R_9)_n$— wherein n is 3, 4, 5 or 6 and $R_8$ and $R_9$ are each independently hydrogen or alkyl; and Z is a boron derivative of the formula $BR_3$, wherein $R_3$ is hydroxy, alkyl, alkenyl, cycloalkyl, cycloalkenyl, alkoxy, carboxyalkyl (preferably having 2 to 19 carbons), carboxyalkenyl (preferably having 4 to 19 carbons), hydroxyalkyl, hydroxyalkenyl, alkoxyalkyl, alkoxyalkenyl, haloalkyl, haloalkenyl, aryl, arylalkyl or $R_4\ R_5$N-alkyl, wherein $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle. See U.S. Pat. No. 4,705,849 (Nunn et al), issued Nov. 10, 1997, which is incorporated by reference.

Other suitable radioactive metal ion binding moieties for use in the present invention include those disclosed in U.S. Pat. No. 5,480,970 (Pollack), issued Jan. 2, 1996; U.S. Pat. No. 5,574,140 (Pollack et al), issued Nov. 12, 1996; U.S. Pat. No. 5,659,041 (Pollack et al), issued Aug. 19, 1997; U.S. Pat. No. 5,720,934 (Dean et al), issued Feb. 24, 1998; and U.S. Pat. No. 5,849,261 (Dean et al), issued Dec. 15, 1998, all of which are incorporated by reference.

The dermatan sulfate useful in the present invention has more than about 25%, preferably more than about 50%, repeating L-iduronic acid→4,6-di-O-sulfated N-acetyl-D-galactosamine disaccharide units, and typically having a molecular weight of from about 1,000 Daltons to about 60,000 Daltons. Particularly preferred dermatan sulfates useful in the present invention have more than about 75%, preferably more than about 90%, repeating L-iduronic acid→4,6-O-disulfated-N-acetyl-D-galactosamine disaccharide units, and are disclosed in U.S. Pat. No. 5,922,690 (Van Gorp et al), issued Jul. 13, 1999, which is incorporated by reference. These preferred dermatan sulfates (hereinafter to as "dermatan disulfate" or "DDS") comprise a mixture of dermatan polymeric chains principally containing connected disulfated disaccharide dimers obtained by chemical sulfation of native dermatan sulfate (primarily L-iduronic acid→N-acetyl-D-galactosamine-4-O-sulfate) that comprises primarily repeating L-iduronic acid→N-acetyl-D-galactosamine-4,6-O-disulfated disaccharide units. Preferably, DDS has an average molecular weight ranging of from about 2,500 to about 37,500 Daltons, preferably from about 5,000 to about 30,000 Daltons, corresponding to about 6 to about 100 monosaccharide units in the polymeric chains. The DDS having an average molecular weight less than about 30,000 Daltons is preferably obtained by cleaving longer chain polysaccharides of: (1) native dermatan sulfate (hereinafter referred to as "native DS") followed by site-specific sulfation of the N-acetyl-D-galactosamine 4-O-sulfate ring at the 6-O hydroxyl to yield primarily the 4,6-O-disulfated disaccharide, or (2) by depolymerization of the DDS. Dermatan chains can be depolymerized by a variety of enzymatic and chemical methods known to those skilled in the art, including those disclosed in U.S. Pat. No. 5,922,690, supra.

The preferred DDS useful in the present invention has significant ATIII-independent antithrombin activity mediated through the action of heparin cofactorII and can be synthesized from commercially obtained DS or preferably native DS according to methods disclosed in U.S. Pat. No. 5,922,690, supra. The preferred DDS can form a salt, where the cation is selected from barium, calcium, copper, lithium, sodium, potassium, zinc, and ammonium ions. See U.S. Pat. No. 5,922,690, supra.

The preferred DDS for use in the present invention has enhanced avidity for surface-associated thrombin. As such, DDS, when covalently attached or bonded to the radioactive metal ion binding moiety to provide the targeted agent, and when reacted, admixed or otherwise combined with a radioactive metal ion (as previously described), can be used to bind, detect, diagnose and treat not only the more advanced vascularized tumors, but also thrombogenic emboli involving a cellular mesh of procoagulant tumor cells, platelets, fibrin and associated bound thrombin at earlier stages of the malignant process. Viewed another way, DDS covalently attached or bonded to the radioactive metal ion binding moiety, acts like a "smart" therapeutic agent in its ability to defeat the tumor cell's cloaking strategy by locking on to the thrombin target bound to the metastatic embolus, thus rendering it visible to detection and potential destruction.

Similarly, DDS covalently attached or bonded to the radioactive metal ion binding moiety is preferred for the detection and treatment of more advanced, vascularized lesions where it is found in association with surface thrombin bound to diseased vasculature of the tumor and to the procoagulant, thrombogenic surface of the malignant cell membrane and fibrin deposits also bound thereto. Thus, in a diagnostic applications, DDS covalently attached or bonded to the radioactive metal ion binding moiety is useful and preferable to the prior alternatives for the imaging, and hence visualization of invading and malignant emboli associated with early lesions of the circulatory phase of the metastatic process as well as intermediate and more advanced stages involving the blood vessels of tumor cell-associated vascularized networks, and procoagulant tumor cell membranes having an activated cell surface thrombin component. In a therapeutic sense, targeting thrombin, by use of DDS covalently attached or bonded to the radioactive metal ion binding moiety, is beneficial and advantageous to the prior alternatives as it seeks out otherwise hidden tumor cells in body residua thus effecting their ablation before becoming established (micro-metastatic foci). DDS covalently attached or bonded to the radioactive metal ion binding moiety is particularly suited to the ablation of the tumor-associated vascular networks that infiltrate and nourish the primary tumor and its more advanced metastatic foci, as well as destroying the outer rim of actively growing cells of high procoagulant activity at the invasion boundary between diseased and normal cell tissues. The preferred localization and accumulation of DDS covalently attached or bonded to the radioactive metal ion binding moiety according to the present invention at sites of diseased and or rejuvenating endothelium having a thrombogenic surface relative to normal, non-diseased endothelium which lacks a thrombogenic surface, is further enhanced by its favorable renal excretion properties and pharmacokinetics. Thus, the enhanced accumulation of DDS covalently attached or bonded to the radioactive metal ion binding moiety at such diseased sites, with negligible diffusion and/or localization to normal endothelium and/or tissues, results in the enhanced imaging of diseased tissues and leads to the stark demarcation and improved visualization of tissue zones formed by the boundaries of diseased and normal tissues. Thus, from a therapeutic perspective, killing is provided up to the rim, or boundary, of this demarcation while minimizing the excessive killing of normal healthy tissues that most often occurs with less specific or non-targeted cytotoxic and radio-pharmaceutical drug approaches.

As thrombin is host-derived and is ubiquitously associated with diseased blood vessels and procoagulant malignant tissues, DDS covalently attached or bonded to the radioactive metal ion binding moiety does not suffer from the disadvantages of targeting heterogeneously expressed tumor cell antigens as with antibody approaches, or limitations to the variety of tumors targeted as with peptide-based ligands to growth factor receptors. Such peptide ligands target growth factor receptors that are narrowly restricted to a few specific tumor cell types, such as those of neuroendocrine origin. Even within a given tumor type, receptors are differentially expressed in their abundance in different tumor cells in a clonally heterogeneous manner which further narrows the scope of their diagnostic and therapeutic utility. In contrast, the DDS covalently attached or bonded to the radioactive metal ion binding moiety according to the present invention is applicable to a broad spectrum of neoplasms as well as a broad scope of arterial and venous coagulapathies such as the aforementioned thrombo-occlusive diseases, thus offering greater advantages to larger patient populations by virtue of a single diagnostic and/or therapeutic formulation of simple composition(s).

The DDS covalently attached or bonded to the radioactive metal ion binding moiety according to the present invention specifically binds to sites of disease wherein activation of the hemostatic mechanism is involved, particularly activated thrombin bound to vessel wall, fibrin and platelet-containing thrombi. Uses of DDS covalently attached or bonded to the radioactive metal ion binding moiety according to the present invention include radiodiagnostic imaging as well as radiotherapy for the treatment of a variety of disease states in which a key component of the pathophysiology involves surface-bound thrombin. By way of example, such disease states include, but are not limited to, thrombo-occlusive disorders such as stroke, myocardial infarction, restenosis, atherosclerosis, peripheral vascular disease, pulmonary embolism, deep vein thrombosis, inflammation due to bacteria and viral infections and oncology.

The dermatan sulfate (preferably DDS) as is, or in a chemically derivatized form, can be covalently attached or bound to the radioactive metal ion binding moiety in a variety of ways, including covalently bonding or attachment via any amino, thio, aldehyde, carboxyl, carboxamide or hydroxyl functional groups present on the radioactive metal ion binding moiety. Dermatan sulfate can be chemically derivatized, by reaction on the dermatan sulfate, with any amino, aldehyde, hydroxyl or carboxyl group present or introduced, to facilitate covalent attachment or bonding to the appropriate functionality on the radioactive metal ion binding moiety. For example, chemical derivatization of the dermatan sulfate can be achieved by periodate oxidation to yield a free reactive aldehyde (see Example 10 of U.S. Pat. No. 5,922,630). The free aldehyde obtained on the iduronic acid moiety of the derivatized dermatan sulfate can be further reacted with ethylene diamine (as a linker) and reduced with sodium cyanoborohydride with the resulting adduct being further reacted in a second step with the radioactive metal ion binding moiety to effect covalent attachment or bonding thereto. This second step can be achieved, for example, by the reaction of the free end group amine on the DDS-linker adduct with an aldehyde functionality introduced into to the radioactive metal ion binding moiety followed by reduction with sodium cyanoborohydride or other suitable reducing agent to stabilize the covalent bond. Alternatively, the free end amine of the DDS-linker adduct can be attached to a reactive carboxyl functionality introduced into the radioactive metal ion binding moiety by the use of the soluble carbodiimide reaction. Chemical derivatization of the dermatan sulfate can also be achieved by reaction with 1-ethyl-3 (3-dimethyl aminopropyl) carbodiimide, N-ethoxycarbonyl-2-ethoxy-1, 2-dihydroquinoline, carbonyldiimidizole, or by other agents known to the art useful for derivatizing similar GAGs in order to facilitate covalent attachment or bonding to the radioactive metal ion binding moiety. See U.S. Pat. No. 5,707,604 (Ranney et al), issued Jan. 13, 1998, which is incorporated by reference, especially Examples 12–16. Hydrazides are particularly useful for attaching the radioactive metal ion binding moiety to the free aldehyde of periodate oxidized DDS, again followed by reduction with sodium cyanoborohydride or other suitable reductants to effect stable bond formation. See Liu et al, "New Approaches for the Preparation of Hydrophobic Heparin Derivatives," *J. Pharm. Sci.* (1994) 83: 1034–1039.

The present invention also provides radiolabeled and/or radioactive composition(s) and agents that can bind to surfaces bearing sites of absorbed thrombin in vivo, methods for preparing such composition(s) and agents and uses of such compositions to reveal and treat such sites in vivo. In particular, the present invention includes compositions and agents, methods for preparing such compositions and agents, as well as the use and formulation of scintigraphic and radiotherapeutic agents for the diagnosis and treatment, respectively, of various disease states having a pathological component of activated thrombin.

In forming active radiolabeled or radioactive diagnostic or therapeutic agents according to the present invention, the radioactive metal ion is reacted, admixed or otherwise combined with the targeted agents of the present invention according to methods well known to those skilled in the radiodiagnostic and radiopharmaceutical art. For example, in forming diagnostic agents from radioactive technetium (Tc) with the targeted agents of the present invention, the Tc, preferably a salt of $^{99m}$Tc pertechnetate, is reacted with the targeted agent of the present invention in the presence of a reducing agent. Preferred reducing agents are dithionite, stannous and ferrous ions; the most preferred reducing agent is stannous chloride. Means for preparing such diagnostic agents are conveniently provided in a kit form comprising a sealed vial containing a predetermined quantity of the targeted agent of the present invention to be labeled and a sufficient amount of reducing agent to label the targeted agent with $^{99m}$Tc. Alternatively, the diagnostic agent can be formed by reacting a reagent of the targeted agent of the present invention with a pre-formed labile complex of Tc and another compound known as a transfer ligand. This process is known as ligand exchange and is well known to those skilled in the art. The labile complex can be formed using such transfer ligands as tartrate, citrate, gluconate or mannitol, for example. Among the $^{99m}$Tc pertechnetate salts useful in the present invention are the alkali metal salts such as the sodium salt, or ammonium salts or lower alkyl ammonium salts.

In a preferred embodiment of the present invention, a kit for preparing Tc- or Re-labeled diagnostic and/or therapeutic agents is provided. An appropriate amount of the targeted agent of the present invention is introduced into a vial containing a reducing agent, such as stannous chloride, in an amount sufficient to label the agent with $^{99m}$Tc, $^{186}$Re or $^{188}$Re. An appropriate amount of a transfer ligand as described (such as tartrate, citrate, gluconate, glucoheptanate or mannitol, for example) can also be included. The kit can also contain conventional pharmaceutical adjunct materials such as, for example, pharmaceutically acceptable salts to adjust the osmotic pressure, buffers, preservatives and the like. The components of the kit can be in liquid, frozen or dry form. In a preferred embodiment, the kit components are provided in lyophilized form. These $^{99m}$Tc, $^{186}$Re or $^{188}$Re labeled radiodiagnostic and radiopharmaceuticals agents according to the present invention can also be prepared by the addition of an appropriate amount of $^{99m}$Tc, $^{186}$Re or $^{188}$Re, or radionuclide complexes thereof, into the vials and reaction under conditions described in Example 2 of U.S. Pat. No. 5,849,261.

Radioactively-labeled scintigraphic imaging agents according to the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to about 100 mCi per mL.

In accordance with the present invention, the $^{99m}$Tc labeled diagnostic and therapeutic agents are administered in a single unit injectable dose. The $^{99m}$Tc labeled diagnostic and therapeutic agents of the present invention can be administered intravenously in any conventional medium for intravenous injection such as an aqueous saline medium, or in blood plasma medium. Generally, the unit dose to be administered has a radioactivity of about 0.01 mCi to about 100 mCi, preferably from about 1 mCi to about 20 mCi. The solution to be injected at unit dosage is typically from about 0.01 mL to about 10 mL. After intravenous administration, imaging in vivo can take place in a matter of a few minutes. However, imaging can take place, if desired, in hours or even longer, after the radiolabeled diagnostic agent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with the present invention.

The present invention can also provide radiolabeled therapeutic agents with cytotoxic radioisotopes such as $^{186}$Re or $^{188}$Re that can be used for radiotherapy of certain tumors as described above. For this purpose, an amount of radioactive isotope from about 10 mCi to about 200 mCi can be administered via any suitable clinical route, preferably by intravenous injection.

The present invention also provides methods for using the diagnostic and radiodiagnostic and therapeutic and radiotherapeutic agents disclosed herein. For radiolabeled embodiments of the agents of the present invention, for example, $^{99m}$Tc labeled scintigraphic imaging agents, an effective diagnostic or therapeutic amount of the diagnostic or radiodiagnostic or therapeutic or radiotherapeutic agent of the present invention is administered. In radiodiagnostic embodiments, localization of the radiolabel is detected using conventional methodologies such as gamma scintigraphy. For the purposes of the present invention, radiotherapy is defined as a therapeutic effect ranging from pain palliation to cure.

The imaging agents provided by the present invention have utility for imaging pathological sites of enhanced thrombogenicity in a mammalian body for diagnostic purposes. The radiotherapeutic agents of the present invention are suitable for the treatment of oncology-related disorders involving a pathological component of activated thrombin.

What is claimed is:

1. A targeted agent having an avidity for thrombin that comprises a dermatan sulfate having more than about 25% repeating L-iduronic acid→4,6-di-O-sulfated N-acetyl-D-galactosamine disaccharide units that is covalently attached to a radioactive metal-ion binding moiety.

2. The agent of claim 1 wherein the dermatan sulfate has more than about 50% repeating L-iduronic acid→4,6-di-O-sulfated N-acetyl-D-galactosamine disaccharide units.

3. The agent of claim 2 wherein the dermatan sulfate has a molecular weight of from about 1,000 Daltons to about 60,000 Daltons.

4. The agent of claim 3 wherein the dermatan sulfate has more than about 75% repeating L-iduronic acid→4,6-di-O-sulfated N-acetyl-D-galactosamine disaccharide units.

5. The agent of claim 4 wherein the dermatan sulfate has a molecular weight of from about 2,500 to about 37,500 Daltons.

6. The agent of claim 4 wherein the iduronic acid moiety of the dermatan sulfate has been derivatized to provide a free aldehyde group capable of being covalently bonded to the radioactive metal-ion binding moiety.

7. The agent of claim 4 wherein the radioactive metal-ion binding moiety has the formula (I):

$$C(p)(aa)C(p) \qquad (I)$$

wherein C is cysteine and (p) is hydrogen or a thiol protecting molecule and (aa) is an amino acid, or a non-amino acid inorganic or an organic molecule that provides a spacer function between Cp residues.

8. The agent of claim 4 wherein the radioactive metal-ion binding moiety has the formula (II):

$$A—CZ(B)—[C(R^1R^2)]_n—X \qquad (II)$$

wherein A is H, HOOC, H$_2$NOC, (dermatan sulfate)-(linker)-NHOC, (dermatan sulfate)-(linker)-OOC or R$^4$, B is H, SH or —NHR$^3$, —N (R$^3$)-(linker)-(dermatan sulfate) or R$^4$; X is SH or —NHR$^3$, —N (R$^3$)-(linker)-(dermatan sulfate) or R$^4$; R$_1$, R$^2$, R3 and R$^4$ are independently H or straight or branched chain or cyclic or cyclic lower alkyl; n is 0, 1, 2; and (1) where B is —NHR$^3$ or —N (R$^3$)-(linker)-(dermatan sulfate), X is SH and n is 1 or 2; (2) where X is —NHR$^3$ or —N (R$^3$)-(linker)-(dermatan sulfate), B is SH and n is 1 or 2; (3) where B is H or R$^4$, A is HOOC, H$_2$NOC, (dermatan sulfate)-(linker)—NHOC or (dermatan sulfate)-(linker)—OOC, X is SH and n is 0 or 1; (4) where A is H or R$^4$, then where B is SH, X is —NHR$^3$ or —NR$^3$-(linker)-

(dermatan sulfate) and where X is SH, B is —NHR³ or —N(R³)-(linker)-(dermatan sulfate); (5) where X is H or R⁴, A is HOOC, H₂NOC, (dermatan sulfate)-(linker)-NHOC or (dermatan sulfate)-(linker)—OOC and B is SH; (6) where Z is methyl, X is methyl, A is HOOC, H₂NOC, (dermatan sulfate)-(linker)—NHOC or (dermatan sulfate)-(linker)—OOC and B is SH and n is 0; and (7) where Z is SH and X is SH, n is not 0; and wherein the thiol moiety is in the reduced form.

9. The agent of claim 4 wherein the radioactive metal-ion binding moiety has formulas (III or IV):

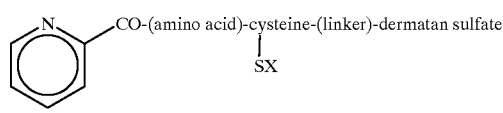

(III)

or,

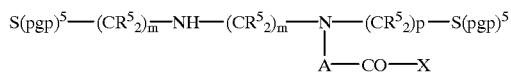

(V)

10. The agent of claim 4 wherein the radioactive metal-ion binding moiety has formulas (V or VI):

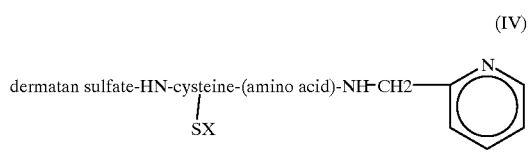

(IV)

wherein each $R^5$ can be independently H, CH₃ or C₂H₅; each $(pgp)^5$ is independently a thiol protecting group or H; m, n, and p are independently 2 or 3; A is a linear or cyclic lower alkyl, aryl, or heterocyclyl, combinations of linear or cyclic lower alkyl, aryl, or heterocyclyl, or substituted linear or cyclic lower alkyl, aryl, or heterocyclyl; and X is (linker)-dermatan sulfate; or

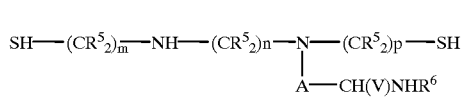

(VI)

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or —CO-(linker)-dermatan sulfate; $R^6$ is H or a (linker)-dermatan sulfate; provided that when V is H, $R^6$ is a (linker)-dermatan sulfate and when $R^6$ is H, V is a —CO-(linker)-dermatan sulfate.

11. The agent of claim 4 wherein the radioactive metal-ion binding moiety has the formula (VII):

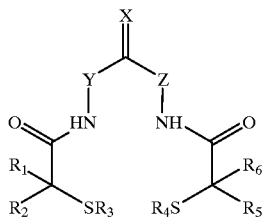

(VII)

wherein $R_1$, $R_2$, $R_5$ and $R_6$ are independently selected from H; carboxyl; lower alkyl; and lower alkyl substituted with a group selected from hydroxyl, sulfhydryl, halogen, carboxyl and aminocarbonyl; or a conjugating group; $R_3$ and $R_4$ are independently selected from H or a sulfur protecting group; X is selected from O, the group $NH_2^+$, or the group $CH_2$ each of which may have attached thereto a conjugating group; Y and Z are independently selected from the group $CR_1R_2$ or $NR_7$; and $R_7$ is selected from H, carboxyl, lower alkyl and lower alkyl substituted with hydroxyl, carboxyl and halogen.

12. The agent of claim 4 wherein the radioactive metal-ion binding moiety has the formula (VIII):

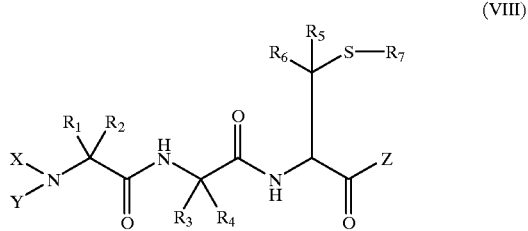

(VIII)

wherein X is a linear or branched, saturated or unsaturated $C_{1-4}$ alkyl chain that is optionally interrupted by one or two heteroatoms selected from N, O and S; and is optionally substituted by one or more substituents selected from halogen, hydroxyl, amino, carboxyl, $C_{1-4}$ alkyl, aryl and C(O)Z; Y is H or a substituent defined by X; X and Y may together form a 5- to 8-membered saturated or unsaturated heterocyclic ring optionally substituted by one or more substituents selected from halogen, hydroxyl, amino, carboxyl, oxo, $C_{1-4}$ alkyl, aryl and C(O)Z; $R_1$ through $R_4$ are selected independently from H; carboxyl; $C_{1-4}$ alkyl; $C_{1-4}$ alkyl substituted with a substituent selected from hydroxyl, amino, sulfhydryl, halogen, carboxyl, $C_{1-4}$ alkoxycarbonyl and aminocarbonyl; an alpha carbon side chain of a D- or L-amino acid other than proline; and C(O)Z; $R_5$ and $R_6$ are selected independently from H; carboxyl; amino; $C_{1-4}$ alkyl; $C_{1-4}$ alkyl substituted by a substituent selected from hydroxyl, carboxyl and amino; and C(O)Z; $R_7$ is selected from H and a sulfur protecting group; and Z is selected from hydroxyl, alkoxy, an amino acid residue, and a linking group.

13. The agent of claim 4 wherein the radioactive metal-ion binding moiety has the formula (IX):

(IX)

wherein X is an anion, Y is a vicinal dioxime of formula (X):

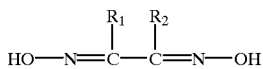

(X)

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are $—(C\ R_8\ R_9)_n—$, wherein n is 3, 4, 5 or 6 and $R_8$ and $R_9$ are each independently hydrogen or alkyl; and Z is a boron derivative of the formula $BR_3$, wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $R_4\ R_5$N-alkyl, wherein $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

14. A kit for preparing a diagnostic and/or therapeutic agent, which comprises predetermined quantity of the agent of claim 4 and a sufficient amount of a the radioactive metal ion.

15. The kit of claim 14 wherein the radioactive metal ion is selected from the group consisting of $^{99m}$Tc, $^{111}$In, $^{67}$Ga, $^{169}$Yb, $^{201}$Tl, $^{153}$Sm, $^{201}$Tl, $^{186}$Re and $^{188}$Re.

16. The kit of claim 15 wherein the radioactive metal ion is $^{99m}$Tc.

17. The kit of claim 15 the radioactive metal ion is selected from the group consisting of $^{186}$Re and $^{188}$Re.

18. A method for radiodiagnostic imaging a disease state associated with surface-bound thrombin activation, which comprises the steps of combining a predetermined quantity of the agent of claim 4 and a sufficient amount of $^{99m}$Tc to form a radiodiagnostic imaging agent, and then administering a diagnostic amount of the radiodiagnostic imaging agent to a person to be diagnosed.

19. A method for radiopharmaceutical treatment of a disease state associated with surface-bound thrombin activation, which comprises the steps of combining a predetermined quantity of the agent of claim 4 and a sufficient amount of a radioactive metal ion selected from the group consisting of $^{186}$Re and $^{188}$Re to form a radiopharmaceutical agent, and then administering a therapeutic amount of the radiopharmaceutical agent to a person to be treated.

20. The agent of claim 4 in combination or administered with heparin cofactor II.

* * * * *